(12) United States Patent
Vecchio

(10) Patent No.: US 6,419,086 B1
(45) Date of Patent: Jul. 16, 2002

(54) RACK FOR MULTICHANNEL PIPETTE CONES

(75) Inventor: Jocelyn Vecchio, Vitry sur seine (FR)

(73) Assignee: Gilson, Inc., Middleton, WI (US)

( * ) Notice: Subject to any disclaimer, the term of this patent is extended or adjusted under 35 U.S.C. 154(b) by 0 days.

(21) Appl. No.: 09/508,258

(22) PCT Filed: Sep. 3, 1998

(86) PCT No.: PCT/FR98/01885

§ 371 (c)(1),
(2), (4) Date: Mar. 8, 2000

(87) PCT Pub. No.: WO99/12646

PCT Pub. Date: Mar. 18, 1999

(30) Foreign Application Priority Data

Sep. 8, 1997 (FR) .............................. 97 11132

(51) Int. Cl.[7] .............................................. B65D 83/10
(52) U.S. Cl. ................... 206/366; 206/443; 206/446; 206/486
(58) Field of Search ................ 206/366, 365, 206/562, 563, 443, 446, 486, 438

(56) References Cited

U.S. PATENT DOCUMENTS

| | | | | | |
|---|---|---|---|---|---|
| 2,557,420 A | * | 6/1951 | Elliott | .......................... | 206/366 |
| 3,643,812 A | * | 2/1972 | Mander et al. | ............... | 211/72 |
| 5,190,169 A | * | 3/1993 | Sincock | ....................... | 206/366 |
| 5,307,933 A | | 5/1994 | Guignet et al. | | |
| 5,392,914 A | | 2/1995 | Lemieux et al. | | |
| 5,642,816 A | * | 7/1997 | Kelly et al. | .................. | 206/486 |
| 5,779,984 A | * | 7/1998 | Kelly et al. | .................. | 206/486 |
| 6,019,224 A | * | 2/2000 | Rich | ........................... | 206/546 |

FOREIGN PATENT DOCUMENTS

| | | |
|---|---|---|
| DE | 27 29 520 A1 | 1/1979 |
| DE | 195 42 921 A1 | 9/1996 |

* cited by examiner

*Primary Examiner*—Shian Luong
(74) *Attorney, Agent, or Firm*—Philip M. Kolehmainen

(57) ABSTRACT

A rack for pipette cones (in particular multichannel cones) includes orifices in a line forming at least one row along at least an alignment direction and a support surface adapted to support cones housed in the orifices. The rack provides for simultaneous access to at least some of the cones in the row. The support surface has a generally convex transverse outline along the alignment direction.

11 Claims, 4 Drawing Sheets

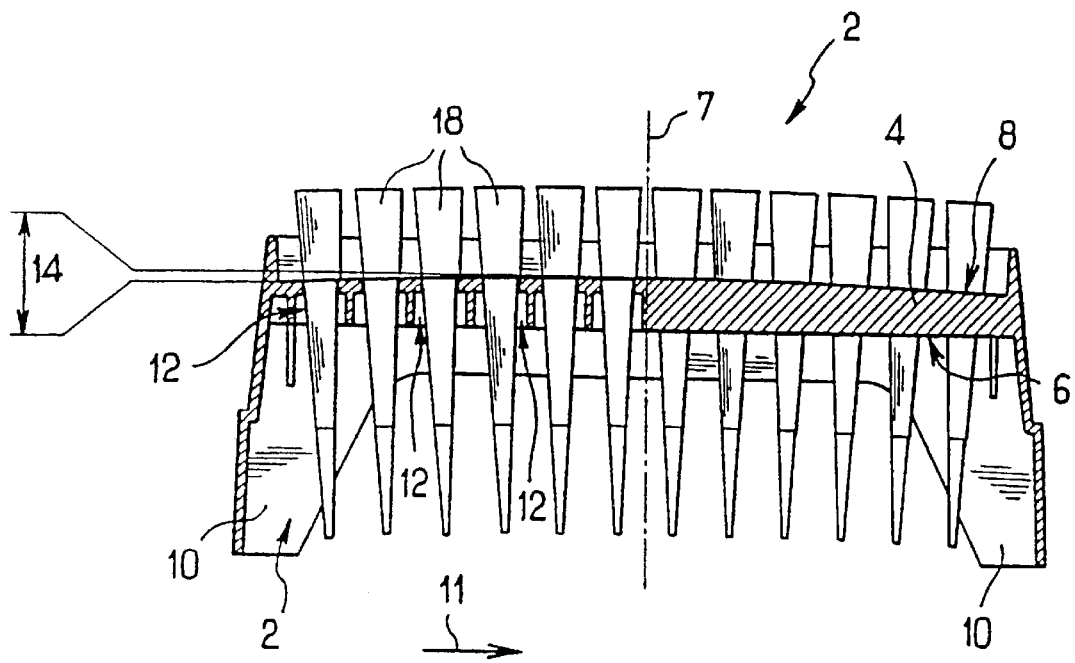
FIG_2
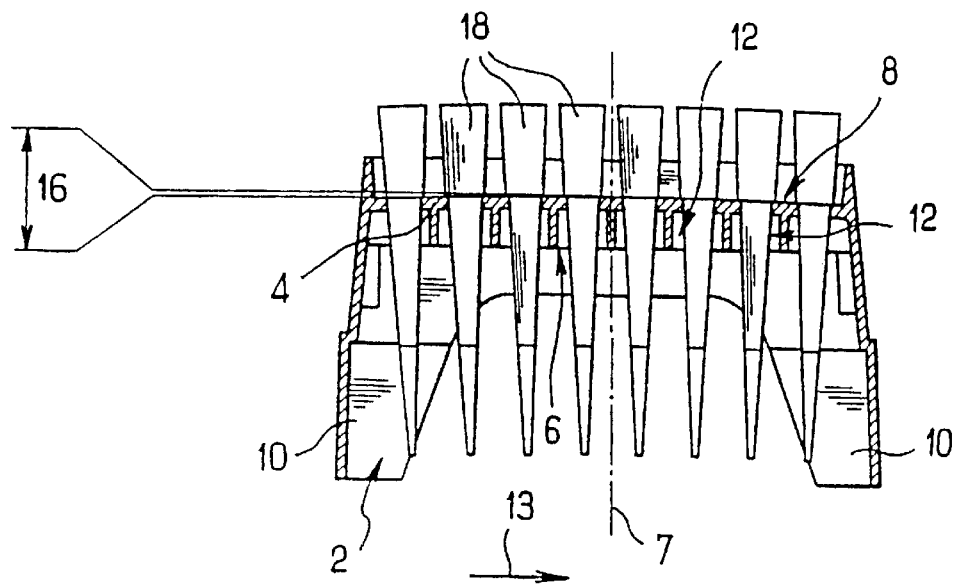
FIG_3

RACK FOR MULTICHANNEL PIPETTE CONES

BACKGROUND OF THE INVENTION

1. Field of the Invention

The present invention relates to a rack for pipette cones, in particular for multichannel pipettes.

2. Background of the Invention

Racks presenting a plane support surface in which orifices are provided in a rectangular matrix are known, e.g. from document U.S. Pat. No. 3,494,210. A rack of that type can receive cones in the orifices, with each cone having, for example, a shoulder suitable for bearing on the support face. The rack enables a plurality of cones to be fixed to the row of endpieces of a multichannel pipette. Since the spacing between the endpieces corresponds to that of the cones received in the rack, the pipette is placed in such a manner that all of its endpieces penetrate into respective cones in a row of orifices in the rack. The user then presses the pipette against the rack so that the cones are retained on the endpieces by friction. Thereafter the user moves the pipette away, together with the cones retained on the endpieces. Nevertheless, that technique generally does not give satisfaction. When the user presses the pipette against the rack, the rack sags in the middle of the row of cone-receiving orifices. As a result, either the user does not press hard enough so when the pipette is moved away some endpieces are not carrying cones, in particular endpieces in the middle of the row, or else the user presses hard and as a result even if there is one cone on each endpiece, it will subsequently be necessary to pull hard in order to separate the cones from the endpieces, particularly for endpieces at the ends of the row.

In addition, the cones, the rack, and the endpieces naturally have geometrical defects, limited to some extent by manufacturing tolerances. Unfortunately, that gives rise to difficulties when the defects are cumulative in one direction for one endpiece and its associated cone, and in an other direction for another endpiece and its associated cone. This happens for a pipette that possesses a first endpiece whose outside width corresponds to the maximum tolerance and that receives a first cone whose inside diameter corresponds to the minimum tolerance, and a second endpiece of the opposite configuration, i.e. of outside width corresponding to a minimum tolerance receiving a second cone whose inside diameter corresponds to the maximum tolerance. Under such conditions, with the above-mentioned rack, and even when no significant sagging occurs, the first cone will be mounted tightly on the first endpiece well before the second cone is securely mounted on the second endpiece. Since the mutually-contacting faces of the cones and the endpieces are conical, that means that the friction zones between the cones and the endpieces on the first and second endpieces are at different heights. This can be made worse by geometrical faults relating to contact between cones and the support surface. Under such conditions, the greater the geometrical defects in the cones, the endpieces, and the rack, the more difficult it becomes to put cones effectively on all of the endpieces of a given pipette.

SUMMARY OF THE INVENTION

An object of the invention is to mitigate those drawbacks and to provide a rack that makes it possible to fix cones effectively on all of the endpieces of a pipette while requiring only moderate force from the user.

To achieve this object, the invention provides a rack for pipette cones, in particular for a multichannel pipette, the rack having aligned orifices forming at least one row in at least one alignment direction, and a support face adapted to support cones received in the orifices, the rack making the cones of the row accessible simultaneously, the support face having a transverse profile in the alignment direction that is generally convex in shape.

Thus, the convex shape prevents a concave sag appearing while the cones are being fixed on the endpieces. This ensures that cones are fixed properly on all of the endpieces of the pipette, and in particular on the endpieces in the middle of the row. This fixing can be obtained with the user exerting moderate force only. Thereafter, the force that needs to be supplied to separate the cones from the endpieces is likewise moderate. In addition, the rack of the invention avoids the need to manufacture the rack, the endpieces, and the cones to comply with very tight dimensional tolerances. Furthermore, it is not necessary to provide the rack with reinforcing ribs. The rack can thus be manufactured, in particular by molding, in a manner that is fast and of low cost. Also, the rack makes it possible to load each cone on the corresponding endpiece easily and without excessive tightening, without being troubled by any geometrical and dimensional defects of the cones, the endpieces, and the rack. To achieve this, it is sufficient, for example, to use the method of the invention for fixing cones to endpieces by tilting, in the manner described below.

The shape need not be "convex" within the strict meaning of the word, for example it can be convex overall while being concave locally. For example, the profile could be M-shaped or camel-humped. Thus, the profile may present at least one upwardly-projecting zone. The profile can have at least one middle zone, preferably in its center, which is higher than the two ends of the profile. In some cases, the shape can be strictly convex.

Advantageously, the orifices are aligned in two non-mutual parallel alignment directions, the support face having transverse profiles in both alignment directions that are convex in shape.

Thus, depending on the number of endpieces on the pipette, the rack can be used with a row of orifices in one or other of the two alignment directions, while obtaining the same above-mentioned advantages.

Advantageously, the orifices are aligned so as to form at least two rows in two respective non-mutually parallel alignment directions, the rack. making the cones in each row accessible simultaneously.

Advantageously, the profile or at least one of the profiles, is rounded in shape.

Advantageously, the profile, or at least one of the profiles, is in the form of a circular arc.

This shape is particularly effective for providing a good distribution of forces on the endpieces for fixing each cone by friction.

Advantageously, the support face is spherical in shape.

Advantageously, the profile, or at least one of the profiles, is triangular in shape.

Advantageously, the rack is constituted by a plurality of portions that are substantially unmovable relative to one another.

Advantageously, the rack is made as a single piece.

Advantageously, the rack has a support wall defining the support face, and support means connected directly to the support wall and suitable for supporting it by resting on a base.

Advantageously, the general shape of the rack is that of a rectangular parallelepiped.

The invention also provides a method of fixing cones on the endpieces of a multichannel pipette in which, starting with a pipette having at least first and second endpieces and with a rack of the invention receiving at least first and second cones in its orifices, the method comprises the following steps:

placing the pipette relative to the rack in such a manner that the profile lies in the same plane as the axes of the endpieces, the first endpiece penetrating into the first cone so as to hold the first cone on the first endpiece, and the second endpiece extending in register with and at a distance from the second cone; and tilting the pipette while keeping the profile in the same plane as the axes of the endpieces so that the first cone held on the first endpiece moves to a distance from the support face and so that the second endpiece penetrate into the second cone so as to hold the second cone on the second endpiece.

This method makes it possible to benefit to a very large extent from the advantages of the rack of the invention. Contrary to the known method in which the pipette is pressed against the rack so as to fix cones simultaneously on all of the endpieces, the method of the invention makes it possible to fix cones successively on the endpieces, endpiece-after-endpiece along the row of cones; The user can thus supply very moderate force which is nevertheless sufficient to put each cone individually into place while simultaneously ensuring that the cone is very well retained by friction on the endpiece.

The invention also provides a method of fixing cones on the endpieces of a multichannel pipette in which, starting from a pipette having at least two endpieces and a rack of the invention receiving at least two cones in its orifices, the method comprises the steps of:

placing the pipette relative to the rack in such a manner that the profile lies in the same plane as the axes of the endpieces, the endpieces penetrating into the respective cones; and urging the pipette towards the rack parallel to the axes of the endpieces so as to retain the cones simultaneously on the respective endpieces.

Thus, in this case, the force provided by the user deforms the support face elastically by flattening its convex shape so as to fix all of the cones effectively to the endpieces.

BRIEF DESCRIPTION OF THE DRAWINGS

Other characteristics and advantages of the invention will appear further on reading the following description of a preferred embodiment given by way of non-limiting example. In the accompanying drawings:

FIGS. 2 and 3 are cross-section views of the FIG. 1 rack respectively on lines II—II and III—III.

DETAILED DESCRIPTION OF THE PREFERRED EMBODIMENT

Figure 1:
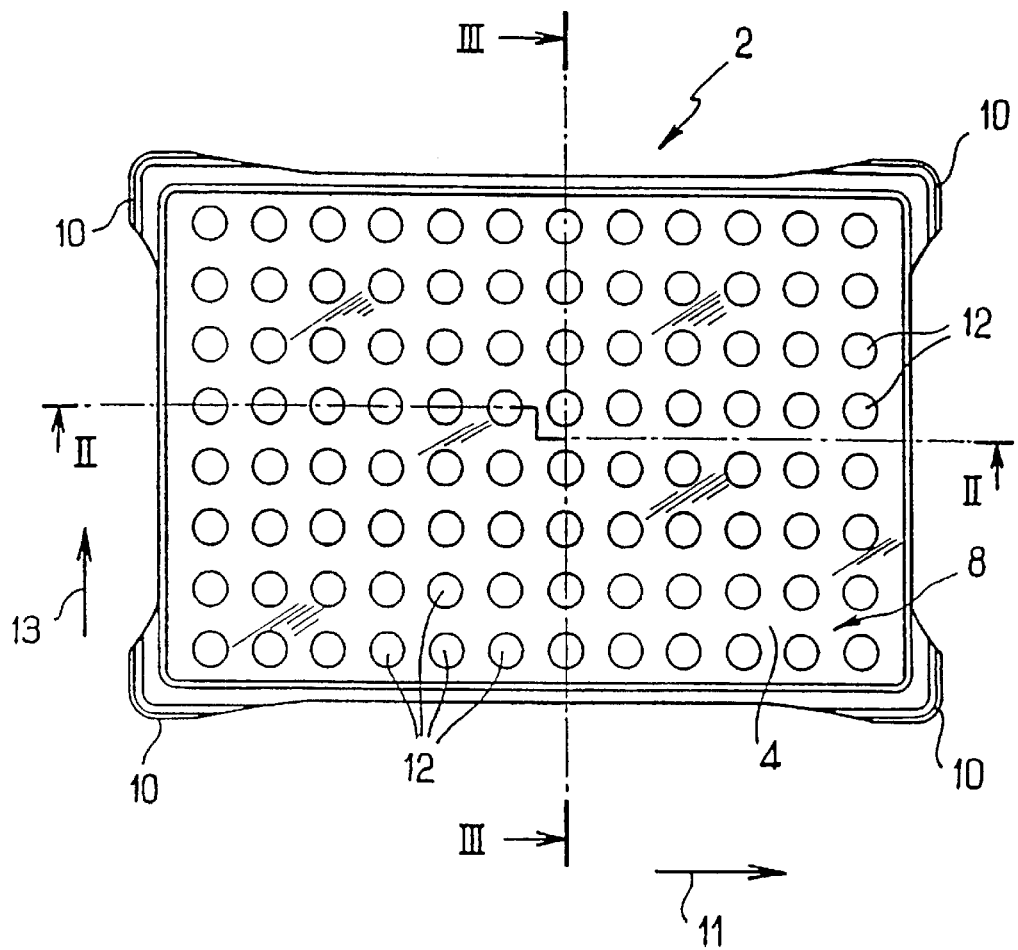
FIG. 1 is a plan view of a rack constituting a preferred embodiment of the invention.

With reference to FIGS. 1 to 3, the rack 2 comprises a support 4 of generally plane shape, being rectangular in plan, and having a bottom face 6 and a top face 8. The rack has four legs 10 secured to the support 4 projecting from its bottom face 6 from the four corners of the rectangle, and suitable for supporting the rack on a horizontal plane.

The support 4 has orifices 12 passing through the thickness of the support from its top face 8 to its bottom face 6. The orifices 12 are disposed in a rectangular matrix and are thus aligned in a plurality of rows in two alignment directions, namely a longitudinal direction 11 and a lateral direction 13, with these two directions being mutually perpendicular in this case. Specifically, the matrix has eight orifices 12 per row in the width direction and twelve orifices 12 per row in the length direction. Each orifice 12 comprises a narrow top segment contiguous with the top face 8 and a broad bottom segment following the narrow segment and contiguous with the bottom face 6.

In this case, the bottom face 6 of the rack is plane. Its top face 8 is spherical in shape, with the geometrical center of the sphere being on the leg side of the support 4. Thus, with reference to FIG. 2, the top face 8 has a transverse profile in the longitudinal direction 11 that is convex in shape along each longitudinal row of orifices 12. The shape of the profile is rounded in the form of a bulging circular arc presenting a small hump 14. Similarly, the transverse profile of the face 8 in the lateral direction 12 is of similar shape for each lateral row of orifices 12 having a hump 16, as shown in FIG. 3. By way of example, the radius of the sphere can be equal to 1 meter (m), the diameter of each orifice 12 in the top face 4 can be about 5 mm, and the minimum distance between two orifices 12 in each row can be about 4 mm. The humps 14 and 16 can be about 1 mm to 2 mm in the center of the support. The support has an axis of symmetry that is vertical and that passes through the center of the rectangle.

The rack 2 is adapted to support cones 18 for the endpieces of a pipette, the cones being received in respective orifices 12. The cones 18 are so called because of their generally conical shape, and above all because of the conical shape of their narrow ends. However they are not exactly conical in shape. In particular, each of them has a circular shoulder on its outside face that is wider than the narrow top segment of each orifice 12. Thus, a cone 18 received in an orifice 12 bears via its shoulder against the top face 8 of the support and rests under gravity on said face. The legs 10 are organized in such a manner that when they are placed on a support plane, the narrow ends of the cones 18 beneath the bottom face 6 lie at a distance from the support plane.

Figure 4:
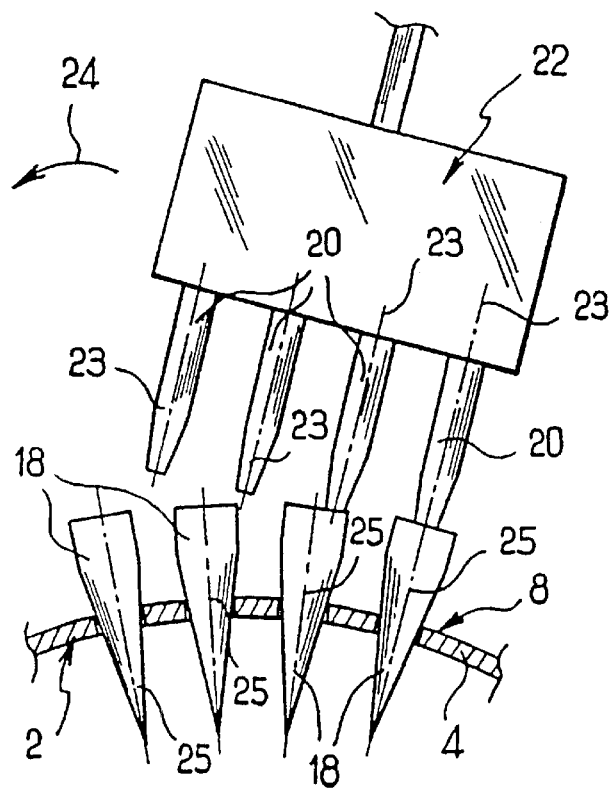
FIGS. 4 and 5 are two fragmentary diagrammatic views of the rack together with a pipette showing how the method of the invention is implemented.
Figure 5:
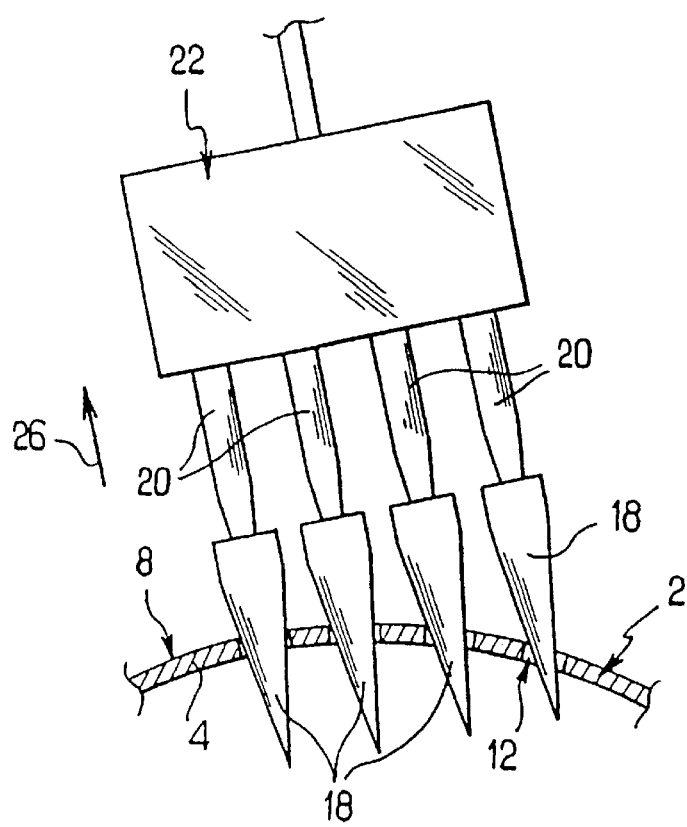

The cones 18 are adapted to be fixed to endpieces 20 of a multichannel pipette 22 as shown diagrammatically in FIGS. 4 and 5. By way of example, such a pipette 22 has eight endpieces 20 having mutually parallel axes and lying in a common plane, with the endpieces being disposed in a row so that their free ends are in alignment. To clarify the drawing, a pipette 22 is shown in FIGS. 4 and 5 that has only four endpieces 20, with the rack of FIGS. 1 to 3 nevertheless being well adapted to a pipette having eight or twelve endpieces, for example. Similarly, to clarify the drawings, the radius of the sphere of the top face 8 is reduced in FIGS. 4 and 5.

The cones 18 are adapted to be held by friction on the free ends of respective endpieces 20 so that liquid can then be sucked up from within the cones and then expelled by means of the pipette.

To fix the cones 18 on the endpieces 20, it is possible to use the method of the invention as shown in FIGS. 4 and 5. By way of example, it is assumed that a pipette 22 is being used that has eight endpieces 20 (of which only four are shown).

It is assumed that one of the lateral rows of eight orifices 12 in the rack has received cones 18. The pipette 22 is placed relative to the rack in such a manner that the first endpiece 20 situated at one end of the row penetrates far enough into the first cone 18 situated at the end of the row of cones to enable said cone to be held by friction on the endpiece. In addition, all of the other endpieces 20 extend in register with respective other cones 18, and possibly penetrate partially therein. The last endpiece 20 at the other end of the row of endpieces is at a distance from the corresponding cone 18. The orifices 12 and the endpieces 20 have effective axes 25 and 23. The profile of the face 8 and the axes 23 and 25 lie in a common vertical plane parallel to the lateral direction 13.

The pipette 22 is then tilted as represented by arrow 24 about a horizontal axis perpendicular to the plane of FIGS. 4 and 5 and perpendicular to the plane common to the axes of the cones and the axes of the endpieces. During this tilting, the profile of the face 8, the axes 25 of the orifices 12, and the axes 23 of the endpieces 20 all remain in the same plane. The titling is performed in such a manner that the first cone 18 is progressively extracted from its orifice 12 in the rack while the last endpiece 20 moves towards its cone 18 so as to penetrate therein and retain it by friction. During this movement, all of the intermediate endpieces 20 of the row penetrate successive into the respective cones 18 and retain them by friction so as to extract them from the corresponding orifices 12. At the end of this tilting movement, as shown in FIG. 5, all of the cones 18 are held by friction on the endpieces 20 and only the last cone 18 of the row of cones and associated with the last endpiece 20 of the row of endpieces is still retained in the original manner in its orifice 12. It then suffices to move the pipette 22 away from the rack 2, parallel to the axes of its endpieces, along arrow 26 in FIG. 5. Because each endpiece 20 is inserted into the associated cone 18 and is fixed thereto by friction individually and in succession, the user need supply only a moderate amount of force for the purpose of fixing the cones.

Because of the convex shape in the longitudinal direction 11, the rack 2 can also be used in the same manner for fixing cones 18 to endpieces in the longitudinal direction 11 of the rack, for example if the pipette 22 has nine to twelve endpieces, with this being done by using any one of the longitudinal rows of orifices 12.

Alternatively, it is possible to fix the cones 18 to the endpieces 20 in simultaneous manner, i.e. by inserting all of the endpieces 20 of the row of endpieces at the same time into the associated cones 18 of the row of cones, and exerting a single vertical force downwards on the pipette 22 so as to cause all of the cones to be held simultaneously on the pipette. Advantage is then taken of the ability of the top face 8 to deform elastically.

Naturally, numerous modifications can be made to the invention without going beyond the ambit thereof.

The top face 8 of the support can have a transverse profile that is convex in a single direction only, in which case the cones 18 need to be fixed to the endpieces 20 in rows that are parallel to said direction. Thus, the top face 8 could be cylindrical. The profile could be rounded without being a circular arc.

Figure 6:
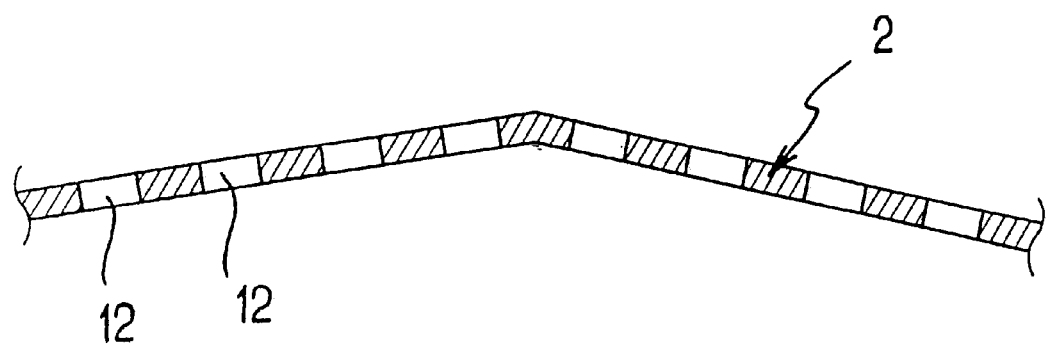
FIG. 6 is a cross sectional view of an alternate shape for the support surface of the rack of FIG. 1.

As is illustrated in FIG. 6, the profiles could be triangular, in the form of upside-down V-shapes, with the top face 8 then having the shape of the tip of a diamond, for example.

What is claimed and desired to be secured by Letters Patent of the United States is:

1. A rack for pipette cones, the rack having aligned orifices forming at least one row in at least one alignment direction, and a support face adapted to support the cones received in the orifices, the rack making the cones of the cones row accessible simultaneously, and being characterized in that the support face has a transverse profile in the at least one row of the at least one alignment direction that is generally convex in shape.

2. A rack according to claim 1, characterized in that the orifices are aligned so as to form at least two rows in two nonparallel alignment directions, the rack making the cones in each row accessible simultaneously.

3. A rack according to claim 1, wherein the orifices are aligned in two nonparallel alignment directions, the support face having transverse profiles in both said nonparallel alignment directions that are convex in shape and characterized in that at least one of the profiles is in the form of a portion of an arc of a circle.

4. A rack according to claim 1, characterized in that the support face is in the shape of a segment of a sphere.

5. A rack according to claim 1, wherein the orifices are aligned in two nonparallel alignment directions, the support face having transverse profiles in both said nonparallel alignment directions that are convex in shape and characterized in that at least one of the profiles is triangular in shape.

6. A rack according to claim 1, characterized in that the rack is constituted by a plurality of portions that are substantially unmovable relative to one another.

7. A rack according to claim 1, characterized in that the rack is made as a single piece.

8. A rack according to claim 1, characterized in that the rack has a support wall defining the support face, and support means connected directly to the support wall and suitable for supporting it by resting on a base.

9. A rack according to claim 1, characterized in that the general shape of the rack is that of a rectangular parallelepiped.

10. A method of fixing cones on the endpieces of a multichannel pipette, the method being characterized in that, starting from a pipette having at least first and second endpieces and a rack for receiving at least first and second cones in its orifices, said rack having aligned orifices forming at least one row in at least one alignment direction, and a support face adapted to support the cones received in the orifices, the rack making the cones of the cones row accessible simultaneously, and being characterized in that the support face has a transverse profile in the at least one alignment direction that is generally convex in shape, the method comprises the steps of:

placing the pipette relative to the rack in such a manner that the profiles lies in a same plane as axes of the endpieces, the first endpiece penetrating into the first cone so as to hold the first cone on the first endpiece, and the second endpiece extending in register with and at a distance from the second cone; and tilting the pipette while keeping the profile in the same plane as the axes of the endpieces so that the first cone held on the first endpiece moves to a distance from the support face and so that the second endpiece penetrate into the second cone so as to hold the second cone on the second endpiece.

11. A rack for pipette cones, the rack having aligned orifices forming at least one row in at least one alignment direction, and a support face adapted to support the cones received in the orifices, the rack making the cones of the cones row accessible simultaneously, and being characterized in that the support face has a transverse profile in the at least one alignment direction that is generally convex in shape, and being further characterized in that the orifices are aligned in two nonparallel alignment directions, the support face having transverse profiles in both said nonparallel alignment directions that are convex in shape.

* * * * *